(12) United States Patent
Walker

(10) Patent No.: US 9,833,268 B2
(45) Date of Patent: *Dec. 5, 2017

(54) REDUCTION JACK FOR SPINAL ROD PLACEMENT AND METHOD OF USE

(71) Applicant: INNOVASIS, INC., Salt Lake City, UT (US)

(72) Inventor: Brandon Walker, Layton, UT (US)

(73) Assignee: Innovasis, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/201,116

(22) Filed: Jul. 1, 2016

(65) Prior Publication Data

US 2016/0367296 A1 Dec. 22, 2016

Related U.S. Application Data

(63) Continuation of application No. 14/448,949, filed on Jul. 31, 2014, now Pat. No. 9,381,051.

(51) Int. Cl.
*A61B 17/70* (2006.01)
*A61B 17/88* (2006.01)

(52) U.S. Cl.
CPC ...... *A61B 17/7086* (2013.01); *A61B 17/7002* (2013.01); *A61B 17/7032* (2013.01)

(58) Field of Classification Search
CPC ............ A61B 17/7082; A61B 17/7037; A61B 17/7076; A61B 17/708; A61B 17/7085; A61B 17/7091; A61B 17/7086; A61B 17/7002; A61B 17/7032

USPC ....... 606/86 A, 279, 104, 99, 914, 264, 275, 606/90, 105
See application file for complete search history.

(56) References Cited

U.S. PATENT DOCUMENTS

| | | | |
|---|---|---|---|
| 7,011,658 B2 | 3/2006 | Young | |
| 8,172,847 B2 | 5/2012 | Dziedzic et al. | |
| 8,377,065 B2 | 2/2013 | Kuntz et al. | |
| 8,377,072 B2 | 2/2013 | Stad et al. | |
| 9,381,051 B2 * | 7/2016 | Walker | A61B 17/7086 |
| 2006/0247649 A1 | 11/2006 | Rezach | |
| 2011/0087298 A1 | 4/2011 | Jones | |
| 2011/0118791 A1 | 5/2011 | Nunley et al. | |
| 2011/0172714 A1 | 7/2011 | Boachie-Adjei et al. | |

* cited by examiner

*Primary Examiner* — Pedro Philogene
*Assistant Examiner* — David C Comstock
(74) *Attorney, Agent, or Firm* — Workman Nydegger

(57) ABSTRACT

A reduction jack for placing a spinal rod within a rod channel of a bone fixation screw includes a mounting stem having a tubular body, a plurality of teeth disposed on the body, a pair of legs projecting from the body, and catches disposed on the legs for engaging the bone fixation screw. A reduction sleeve at least partially encircles the mounting stem. A gear assembly is mounted on the reduction sleeve and engages the teeth on the body such that manipulation of the gear assembly facilitates movement of the reduction sleeve along the mounting stem. A first pawl is pivotably mounted to the reduction sleeve and resiliently biased against the teeth on the body, the first pawl being pivotable between a first position where the first pawl engages the teeth on the body and a second position wherein the first pawl does not engage the teeth on the body.

16 Claims, 15 Drawing Sheets

REDUCTION JACK FOR SPINAL ROD PLACEMENT AND METHOD OF USE

CROSS-REFERENCE TO RELATED APPLICATIONS

This application is a continuation of U.S. application Ser. No. 14/448,949, filed Jul. 31, 2014, which application is incorporated herein by specific reference.

BACKGROUND OF THE INVENTION

1. The Field of the Invention

The present invention relates to reduction jacks used for reducing spinal rods into rod channels of bone fixation screw.

2. The Relevant Technology

There are a number of surgical procedures and treatments that require the immobilization of a portion of the spine. For example, vertebral fusion is a medical procedure where adjacent vertebrae of the spine are fused together. As part of this procedure, a mechanical stabilizing system is implanted in the patient which immobilizes the adjacent vertebrae. Such stabilizing systems can also be used in the treatment of spinal trauma and spinal curvature such as scoliosis.

A typical spinal stabilizing system includes, in part, a plurality of bone fixation screws that are mounted on each side of each consecutive vertebra that is being fused together. Each bone fixation screw has a collar with a U-shaped rod channel formed thereon. An elongated, metal, spinal rod is received within the rod channels of the aligned bone fixation screws on each side of the spine. Once the spinal rods are positioned, fasteners are threaded onto the collars so as to rigidly lock the spinal rods to the bone fixation screws, thereby securing each vertebra in a fixed relative location.

Because the vertebrae are often out of alignment at the start of the procedure, the spinal rods may freely be received within some of the rod channels of the bone fixation screws but may be misaligned with others. To that end, reduction jacks are used to reduce or move the spinal rods into the rod channels from which the spinal rods are misaligned.

A reduction jack typically includes a base that removably mounts to the bone fixation screw and captures the spinal rod, a reducer that engages the base, and a mechanical drive assembly. The drive assembly is manually operated and is used to move the reducer relative to the base so that the reducer pushes against the spinal rod and forces the spinal rod into the rod channel of the bone fixation screw. Moving the spinal rod into the rod channel can occur as a result of moving the spinal rod and/or the corresponding vertebrae.

Although reduction jacks are useful for their intended purpose, they typically have a number of shortcomings. For example, the drive assembly typically moves the reducer at a very slow rate. As such, it can take an extended period of time to even move the reducer to the point where it initially engages the spinal rod. It can also take an extended time period to move the reducer back to its original position so that the reduction jack can be removed from the bone fixation screw. In addition to being time consuming to use, conventional reduction jacks can be difficult to attach to the bone fixation screws. Likewise, in conventional reduction jacks it can often be difficult to access and/or manipulate the drive assembly that moves the reducer relative to the base. Furthermore, some conventional reduction jacks can obstruct the bone fixation screw making it difficult to align and attach the fastener to the bone fixation screw.

Finally, the reduction jacks can also be used as a lever, when attached to a bone fixation screw, to move the vertebrae to a desired position or orientation. Conventional reduction jacks can often be too long or too short for their desired placement and use.

Accordingly, what is needed in the art are reduction jacks that overcome one or more of the above shortcomings.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements. Furthermore, multiple instances of an element may each include separate letters appended to the element number. For example two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

DETAILED DESCRIPTION OF THE PREFERRED EMBODIMENTS

Figure 1:
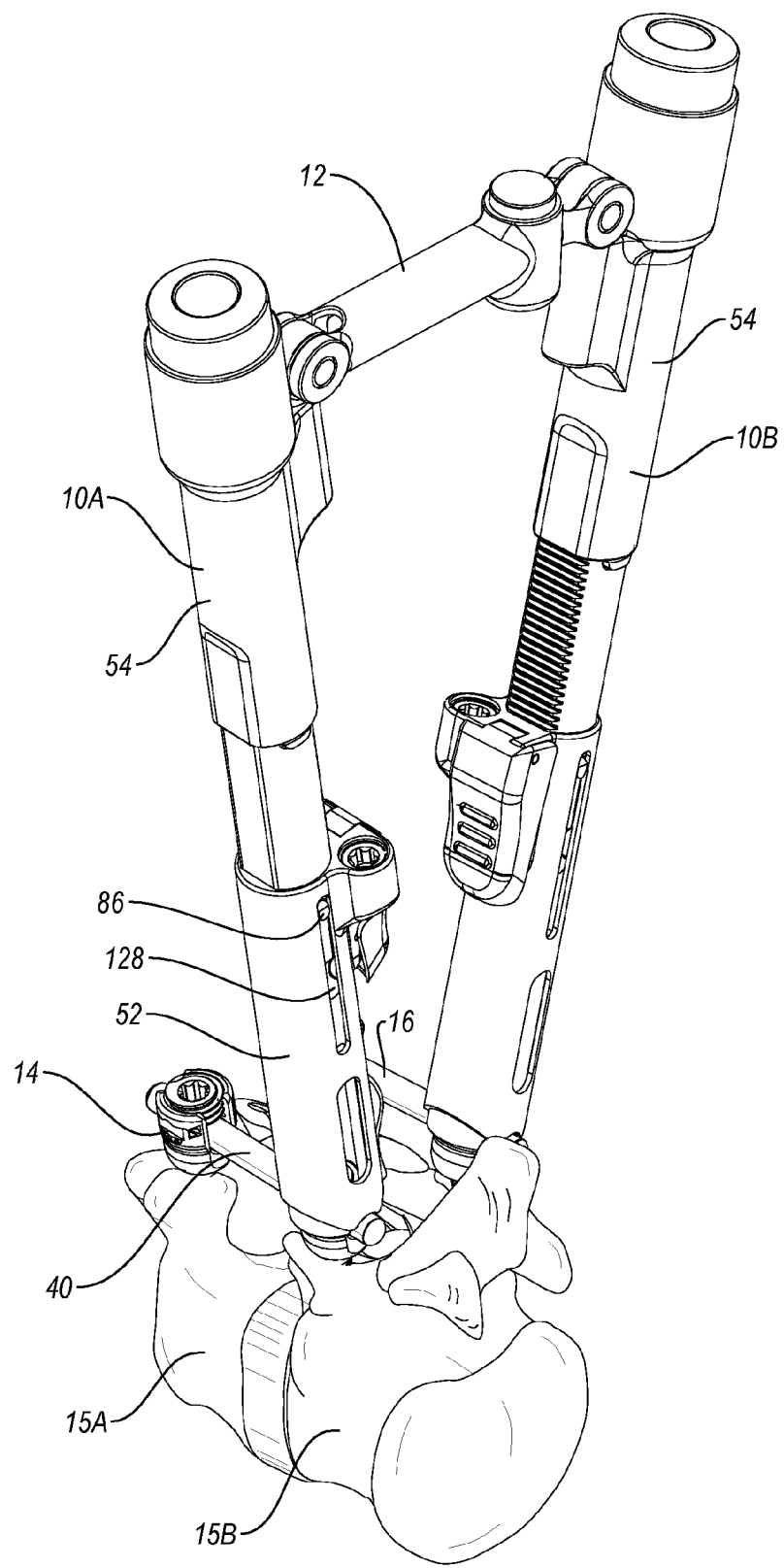
FIG. 1 is a perspective view of a pair of reduction jacks reducing spinal rods into rod channels of bone fixations screws attached to a spine.

In the following detailed description, reference is made to the accompanying drawings, which form a part hereof. In the drawings, similar symbols typically identify similar components, unless context dictates otherwise. The embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein. It will also be understood that any reference to a first, second, etc. element in the claims or in the detailed description is not meant to imply numerical sequence, but is meant to distinguish one element from another unless explicitly noted otherwise.

In addition, as used in the specification and appended claims, directional terms, such as "top," "bottom," "up," "down," "upper," "lower," "proximal," "distal," "horizontal," "vertical," and the like are used herein solely to indicate relative directions and are not otherwise intended to limit the scope of the invention or claims.

Depicted in FIG. 1 is a pair of reduction jacks 10A and 10B coupled together by a bridge 12 and incorporating features of the present invention. Reduction jacks 10 are used in association with bone fixation screws 14 and spinal rods 40. Bone fixation screws 14 are mounted on opposing sides of adjacent vertebrae 15 while spinal rods 40 are secured to and longitudinally extend between aligned bone fixation screws 14. Bone fixation screws 14 and spinal rods 40 are commonly used in procedures for fusing together adjacent vertebrae 15 but can also be used in other spinal applications. In general, reduction jacks 10 are used for reducing spinal rods 40 into rod channels on bone fixation screw 14 and derotating select vertebrae 15 that may be out of alignment.

Figure 2:
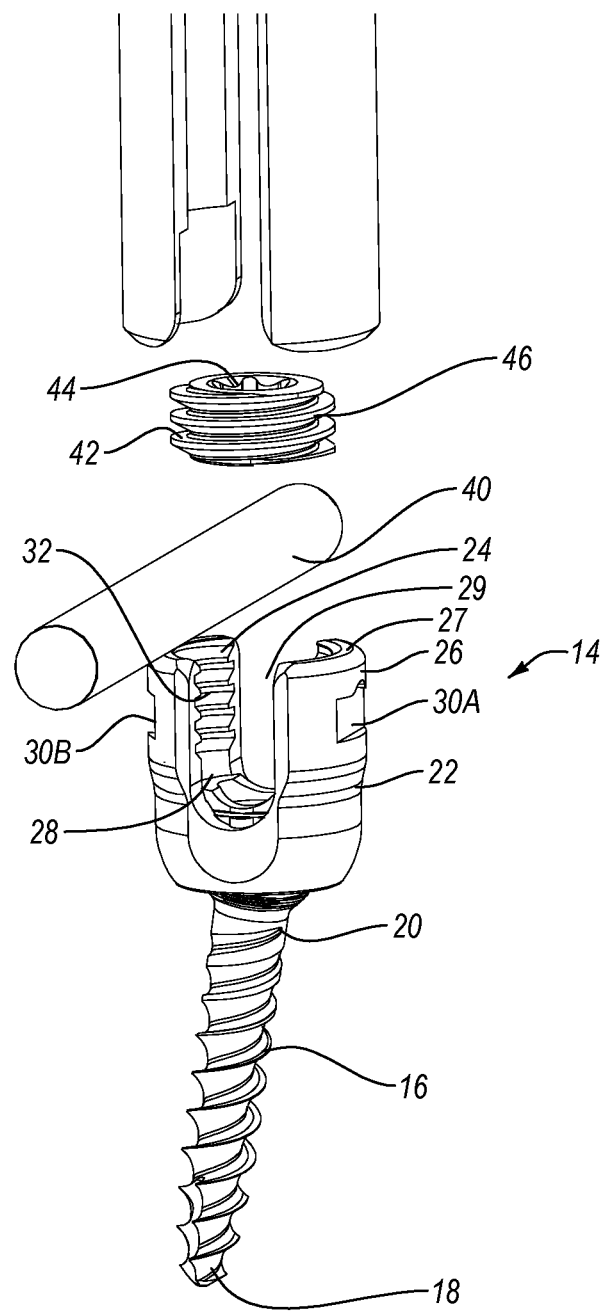
FIG. 2 is a perspective view of the bone fixation screw and spinal rod of FIG. 1.

More specifically, as depicted in FIG. 2, each bone fixation screw 14 comprises a threaded shaft 16 having a tip end 18 configured for threading into a vertebra and an opposing fixation end 20. Disposed on fixation end 20 is a collar 22. Collar 22 can be either pivotally mounted on fixation end 20, as depicted, so as to form a polyaxial screw or can be rigidly fixed on fixation end 20. Collar 22 has an interior surface 24, an exterior surface 26, and a U-shaped rod channel 28 that laterally passes through collar 22. Collar 22 terminates at an end face 27 having an opening 29 formed thereat that communicates with rod channel 28. Recessed on exterior surface 26 on opposing sides of rod channel 28 is a pair of retention notches 30A and 30B. Formed on interior surface 24 on opposing sides of rod channel 28 are threads 32.

Elongated spinal rod 40 typically has a cylindrical configuration and is sized so that it can be received within rod channel 28. A fastener 42 has a top surface with a driver socket 44 formed thereon and a threaded side surface 46 extending along the length thereof. Fastener 42 is configured to be received within opening 29 of collar 22 so that it can be screwed into rod channel 28 by engaging threaded side surface 46 with threads 32. When spinal rod 40 is received within rod channel 28, the engagement of fastener 42 with collar 22 secures spinal rod 40 within rod channel 28. Furthermore, fastener 42 can be further threaded into rod channel 28 until spinal rod 40 is compressed between fastener 42 and either collar 22 or fixation end 20 of shaft 16, thereby fixing spinal rod 40 relative to collar 22. By securing spinal rod 40 to each bone fixation screw 14 located on consecutive vertebrae 15 (FIG. 1), spinal rod 40 fixes the corresponding vertebrae relative to each other. The length of spinal rod 40 can vary depending upon the number of consecutive vertebrae spinal rod 40 is used for securing together. Again, separate spinal rods 40 and corresponding bone fixation screws 12 are used on opposing sides of vertebrae 15.

It is appreciated that bone fixation screws 14 can come in a variety of different designs, configurations, and sizes that can be used with a variety of different types of fasteners. In general, however, all bone fixation screws include a rod channel configured to receive a spinal rod and a fastener that can attach to the bone fixation screw for securing the spinal rod within the rod channel.

Figure 3:
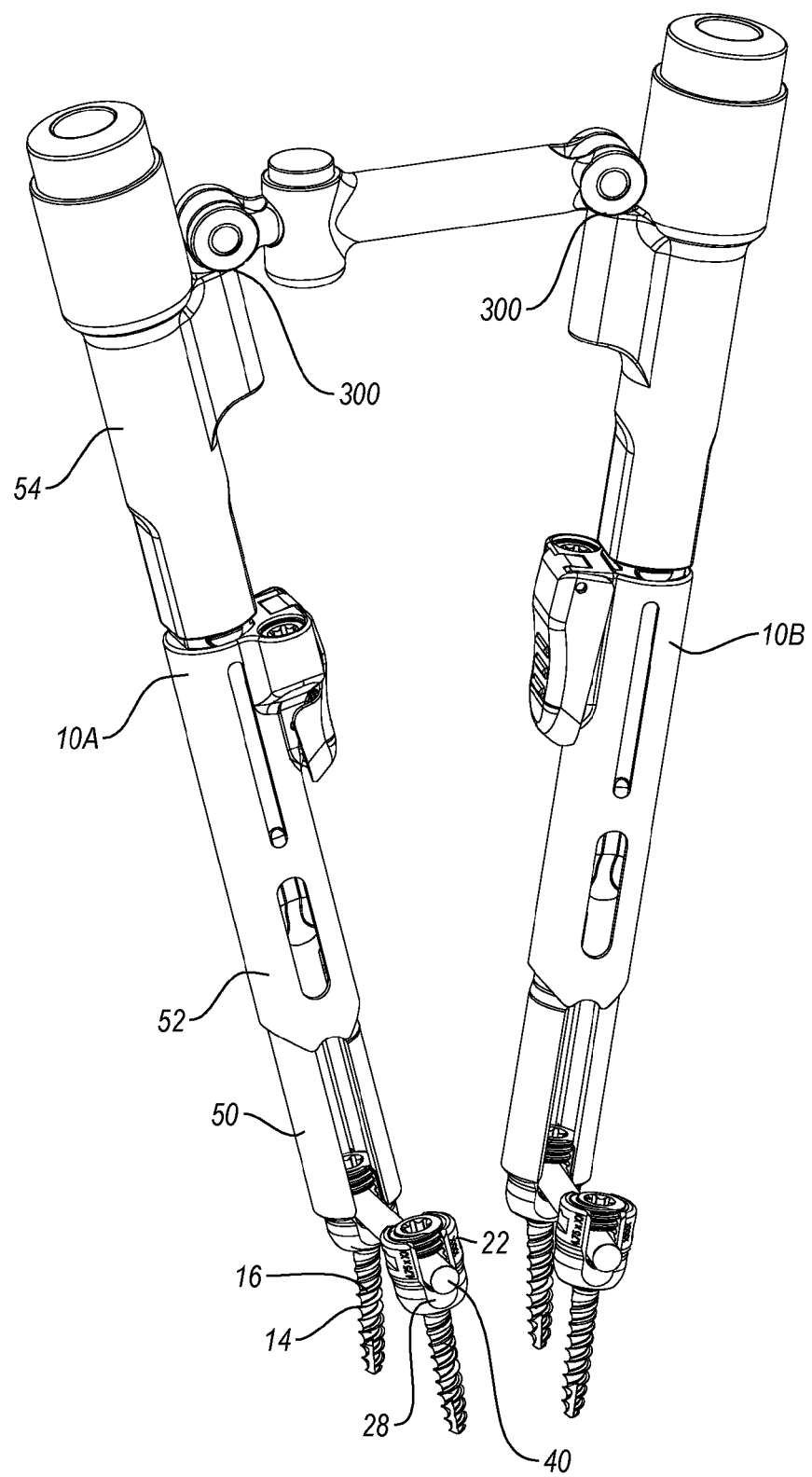
FIG. 3 is a perspective view of the reduction jacks and bone fixation screws of FIG. 1 outside of the spine.
Figure 4:
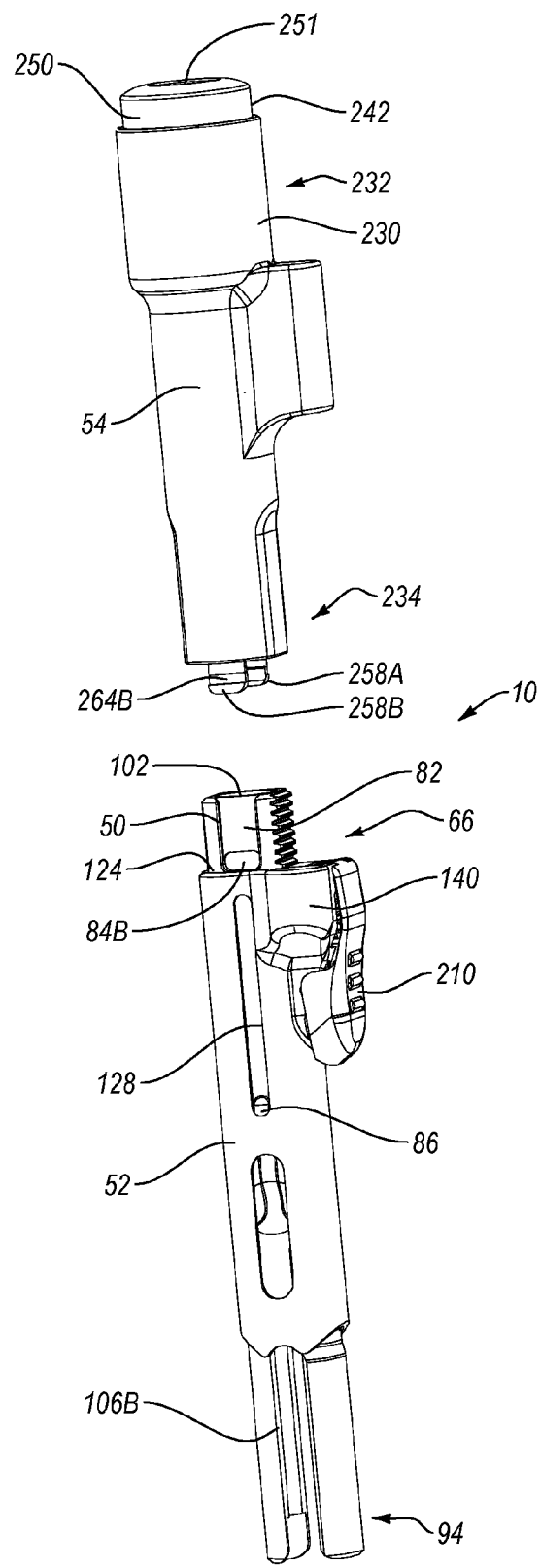
FIG. 4 is a partially exploded view of one of the reduction jacks shown in FIG. 1.
Figure 5:
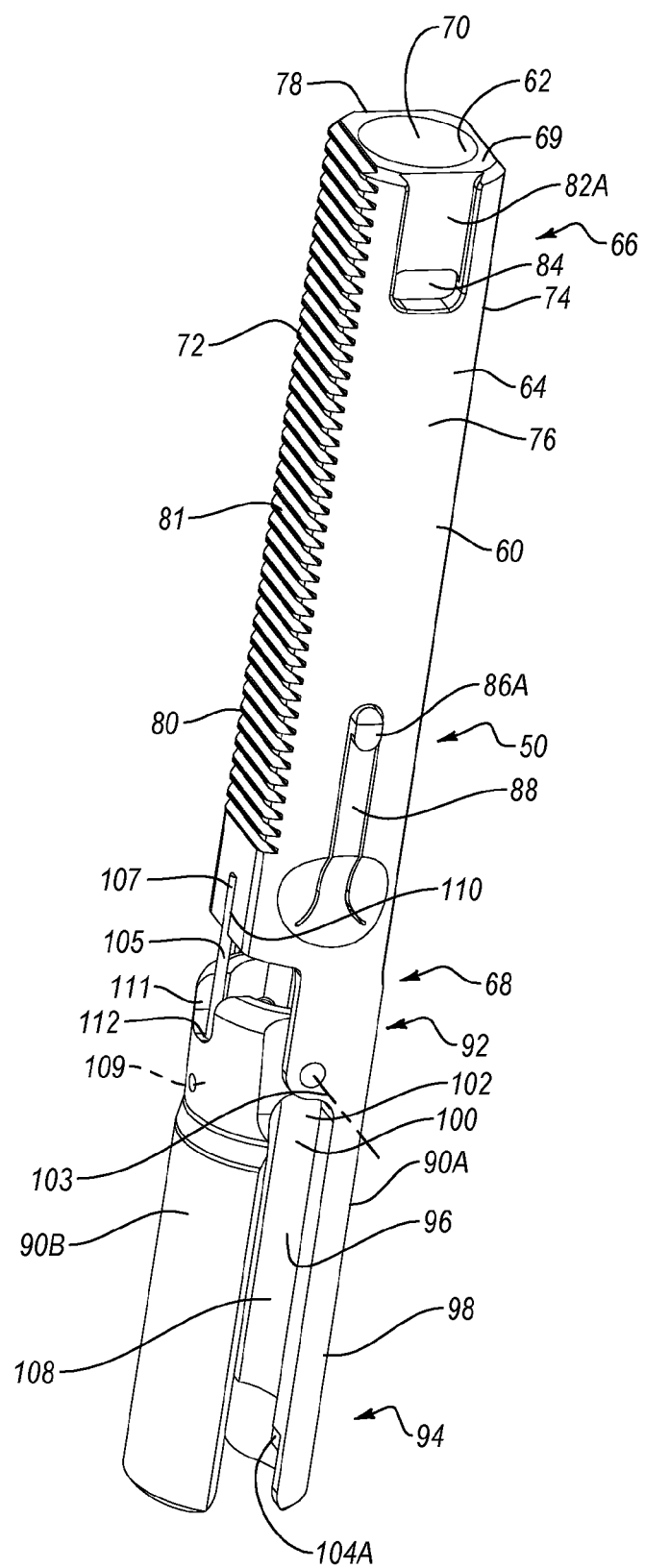
FIG. 5 is an enlarged perspective view of the mounting stem of the reduction jack shown in FIG. 4.

As depicted in FIGS. 3 and 4, reduction jacks 10A and 10B are, in part, used for reducing or moving spinal rod 40 into rod channel 28 of a corresponding bone fixation screw 14. Each reduction jack 10 comprises, in part, an elongated tubular mounting stem 50 that couples with bone fixation screw 14, a reduction sleeve 52 that at least partially encircles and moves along the length of mounting stem 50, and an extension 54 that removably couples with an end of mounting stem 50. As depicted in FIG. 5, mounting stem 50 comprises an elongated tubular body 60 having an interior surface 62 and an exterior surface 64 that longitudinally extend between a proximal end 66 and an opposing distal end 68. Proximal end 66 terminates at a proximal end face 69. Interior surface 62 bounds a passageway 70 longitudinally extending therethrough. Exterior surface 64 includes a front face 72, an opposing back face 74 and side faces 76 and 78 extending therebetween. In one embodiment, each face 72, 74, 76, and 78 is substantially planer so that exterior surface 64 has a substantially square or rectangular transverse cross section with the intersecting corners being rounded or chamfered. Formed along front face 72 are a plurality of teeth 80 that are orientated so as to longitudinally extend between side faces 76 and 78. Teeth 80 combine to form a rack 81 that typically extends over a majority of the length of front face 72 and typically extends at least 50% of the length or more commonly at least 70% or 80% of the length.

Figure 6:
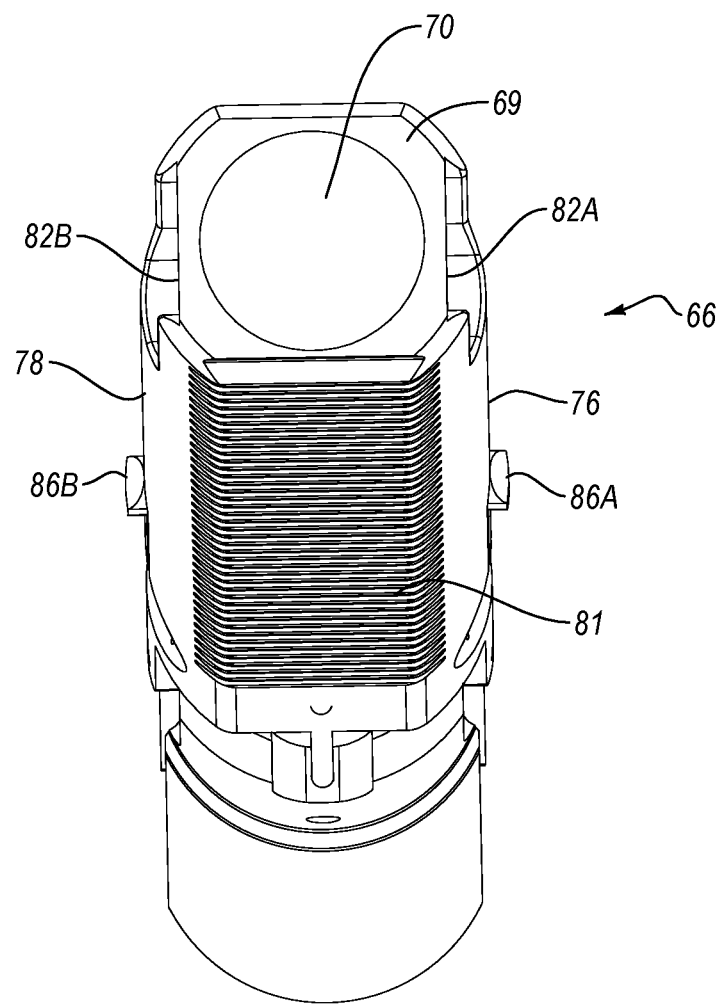
FIG. 6 is a perspective view of the proximal end of the mounting stem shown in FIG. 5.

As depicted in FIG. 6, a pair of locking channels 82A and 82B longitudinally extend along a length of side faces 76 and 78 at proximal end 66, respectively, and intersect with proximal end face 69. A pocket 84 (FIG. 5) is further recessed at the distal end of each alignment channel 82. Guide post 86A and 86B outwardly project from side faces 76 and 78, respectively, at or towards distal end 68. Each guide post 86 projects from a partially cut out section 88 (FIG. 5) of body 60. Section 88 flexes relative to the remainder of body 60 so that guide post 86 are resiliently flexible relative to side faces 76 and 78. That is, guide post 86 can be pressed into side faces 76 and 78 and will then resiliently rebound to project out from side faces 76 and 78.

Figure 7:
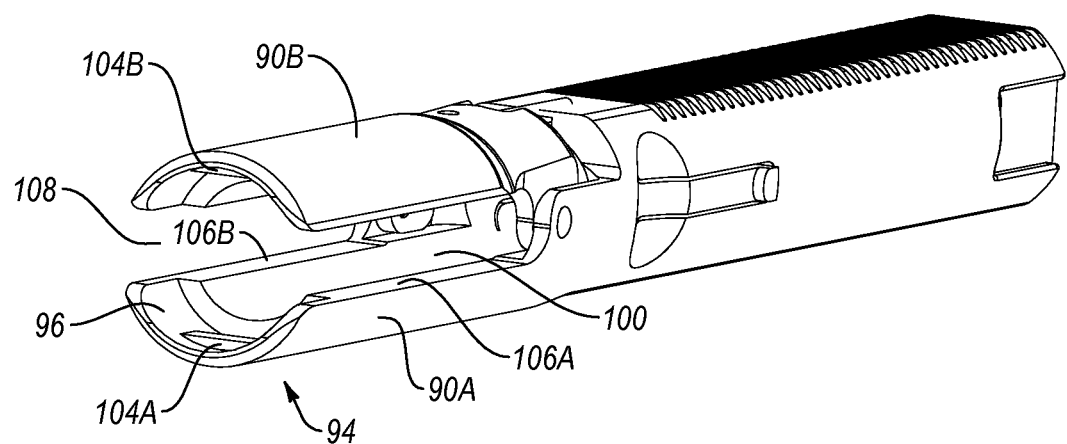
FIG. 7 is a perspective view of the distal end of the mounting stem shown in FIG. 5.

Returning to FIG. 5, projecting from distal end 68 of body 60 are a pair of legs 90A and 90B. Each leg has a proximal end 92 and an opposing distal end 94. Proximal end 92 of leg 90A is rigidly fixed to distal end 68 of body 60. For example, in one embodiment leg 90A is integrally formed as a signal unitary member with body 60. In contrast, proximal end 92 of leg 90B is hingedly coupled to distal end 68 of body 60 so as to have a pivot axis 103. As such, distal end 94 of leg 90B can pivot outward and away from leg 90A by pivoting about axis 103. Legs 90A and 90B both have an interior surface 96 and an opposing exterior surface 98 extending between opposing ends 92 and 94. Interior surface 96 of legs 90A and 90B bound a passageway 100 therebetween that extends along the length of legs 90. Passageways 70 and 100 are longitudinally aligned and are in communication with each other so that they jointly form a passageway 102 that extends the full length of mounting stem 50 from proximal end 66 to distal end 94. As depicted in FIG. 7, radially inwardly projecting from interior surface 96 of each leg 90A and 90B at distal end 94 is a catch 104A and 104B, respectively. As will be discussed below in greater detail, catches 104 are configured to be received within retention notches 30 (FIG. 2) on bone fixation screws 14 to enable legs 90 to firmly engage bone fixation screws 14. In one embodiment of the present invention, means are disposed on legs 90 for engaging bone fixation screws 14. One example of such means is catches 104. In alternative embodiments, however, catches 104 can come in a variety of different configurations and can be placed in a variety of different orientations and positions on legs 90 depending on the configuration, position, and orientations of retention notches 30 located on bone fixation screws 14.

U-shaped slots 106A and 106B are formed between the two pairs of adjacent side edges of legs 90A and 90B. Slots 106A and B and passageway 100 combine to form a rod channel 108 that transversely extends between legs 90A and 90B and which is configured to receive spinal rod 40.

In one embodiment of the present invention, means are provided for applying a force that resiliently urges distal ends 94 of legs 90A and 90B away from each other. By way of example and not by limitation, a spring 105 is provided having a first end 107 and an opposing second end 109. Spring 105 is in the form of an elongated rod comprised of a resiliently flexible material, such as a metal, which is curved or bent in its relaxed state. First end 107 of spring 105 is secured to body 60 at distal end 68 of front face 72. First end 107 can be secured such as by being welded or press-fit on body 60. First end 107 can also be received within an opening on body 60 or otherwise secured thereto. A notch 111 is recessed at proximal end 92 of leg 90 and second end 109 of spring 105 is received within an opening 110 formed on an inside face of notch 111.

When legs 90A and 90B are received within reduction sleeve 52, as shown in FIG. 1, legs 90A and 90B are moved into parallel alignment as shown in FIG. 5. In this parallel alignment, spring 105, which naturally has a curve or bend, is moved to a more linear configuration so that spring 105 applies a force to leg 90B that wants to resiliently urge distal ends 94 of legs 90A and 90B away from each other. Specifically, the force urges leg 90B to pivot about axis 103 away from leg 90A. Accordingly, when reduction sleeve 52 is removed from off of legs 90, as discussed below, legs 90 resiliently separate. This enables collar 22 of bone fixation screw 14 (FIG. 2) to be easily placed between legs 90 for engaging therewith. It is appreciated that a variety of different spring configuration can be used to urge separation of legs 90. For example a coil spring could extend between body 60 and leg 90B which stretches as legs 90 are moved into parallel alignment. Other spring configurations can also be used.

In an alternative embodiment, it is appreciated that leg 90A can also be hingedly mounted to body 60. Likewise, a separate spring 105 can be coupled with leg 90A to apply a force the urges leg 90A to pivot away from leg 90B. In another alternative embodiment, it is appreciated that spring 105 need not be coupled with leg 90B. In this embodiment, leg 90B can be manually pivoted during attachment to bone fixation screw 14.

Figure 8:
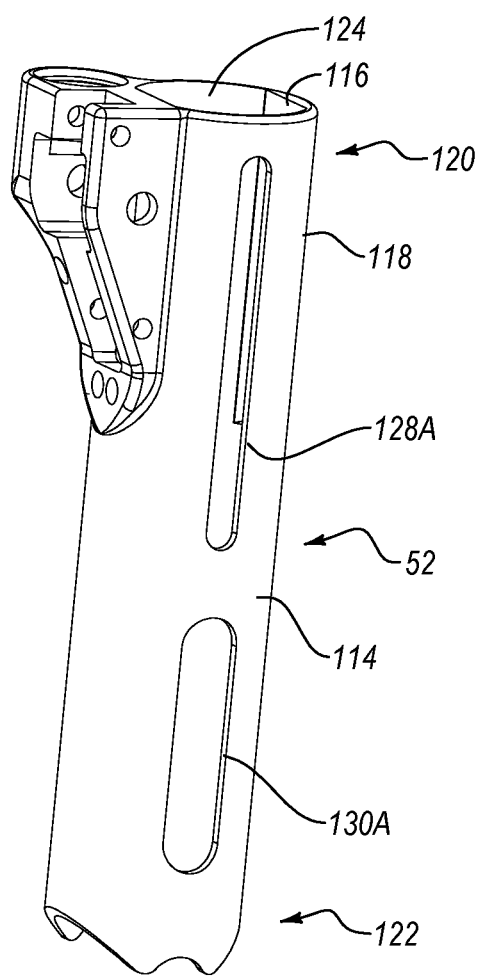
FIG. 8 is a perspective view of the side of the reduction sleeve of the reduction jack shown in FIG. 4.

Turning to FIG. 8, reduction sleeve 52 comprises a tubular member 114 having an interior surface 116 and an exterior surface 118 that longitudinally extend between a proximal end 120 and an opposing distal end 122. Interior surface 116 bounds a passage 124 that is configured to receive mounting stem 50 as depicted in FIG. 4. Continuing with FIG. 8, elongated guide slots 128A and 128B (FIG. 9) are longitudinally aligned on opposing sides of tubular member 114 so as to communicate with passage 124. Guide slots 128 are configured to receive guide post 86 (FIG. 5) of mounting stem 50.

Specifically, as depicted in FIG. 4, when mounting stem 50 is received within passage 124 of reduction sleeve 52, guide post 86A and B are received within locking slots 128A and B, respectively. Reduction sleeve 52 can then move linearly along mounting stem 50 between a first or raised position as shown in FIG. 4 where guide posts 86 are located at the distal end of guide slots 128 and a second or lowered position as shown in FIG. 1 where guide posts 86 are located at the proximal end of guide slots 128. Guide posts 86 and guide slots 128 thus both limit the longitudinal movement of reduction sleeve 52 along mounting stem 50 so that reduction sleeve 52 does not unintentionally become disengaged from mounting stem 50 and keep reduction sleeve 52 properly oriented on mounting stem 50. That is, posts 86 prevent reduction sleeve 52 from rotating about mounting stem 50. Although reduction sleeve 52 is shown as being circular so that it complete encircles mounting stem 50, in an alternative embodiment reduction sleeve 52 can have a C-shaped transverse cross section.

Also formed on tubular member 114 are viewing slots 130A and B that are formed distal of guide slots 128. Viewing slots 130 are in longitudinal alignment with guide slots 128 and extend through tubular member 114 so as to communicate with passage 124.

Figure 9:
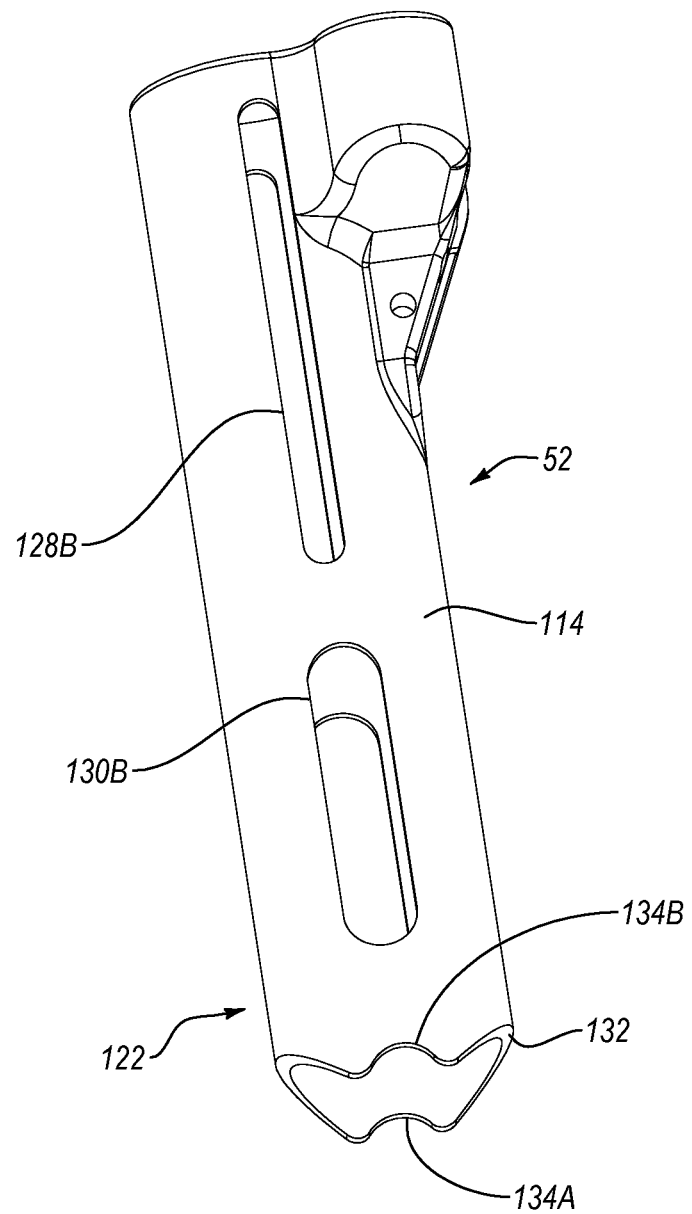
FIG. 9 is a perspective view of the distal end of the reduction sleeve shown in FIG. 8.

As depicted in FIG. 9, distal end 122 of tubular member 114 terminates at a distal end face 132 that has a pair of arched engagement grooves 134A and B formed thereon. Engagement grooves 134 are used to receive spinal rod 40 in positive engagement so that reducing sleeve 52 can more efficiently be used in reducing spinal rod 40 into rod channel 28 (FIG. 2) of bone fixation screw 14.

Figure 10:
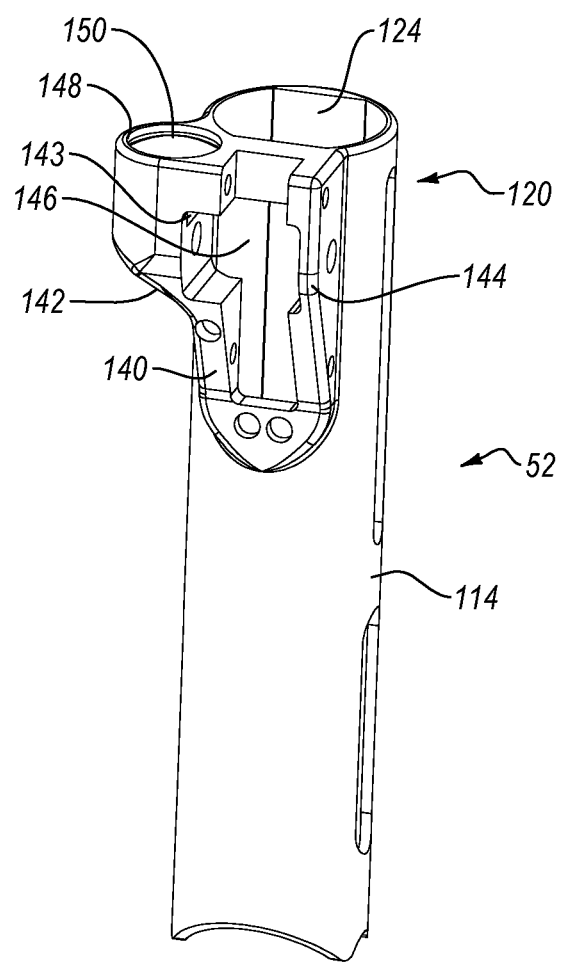
FIG. 10 is a perspective view of the front of the reduction sleeve shown in FIG. 8.

Turning to FIG. 10, mounted on proximal end 120 of tubular member 114 is a housing 140. In general, housing 140 includes a first arm 142 and a second arm 144 that longitudinally extend along tubular member 114. Mounted between arms 142 and 144 is a compartment 146 that extends through tubular member 114 so as to communicate with passage 124. First arm 142 terminates at a proximal end face 148 and bounds a pocket 150. Pocket 150 extends longitudinally down first arm 142 and laterally communicates with compartment 146 through a side opening 143.

Figure 11:
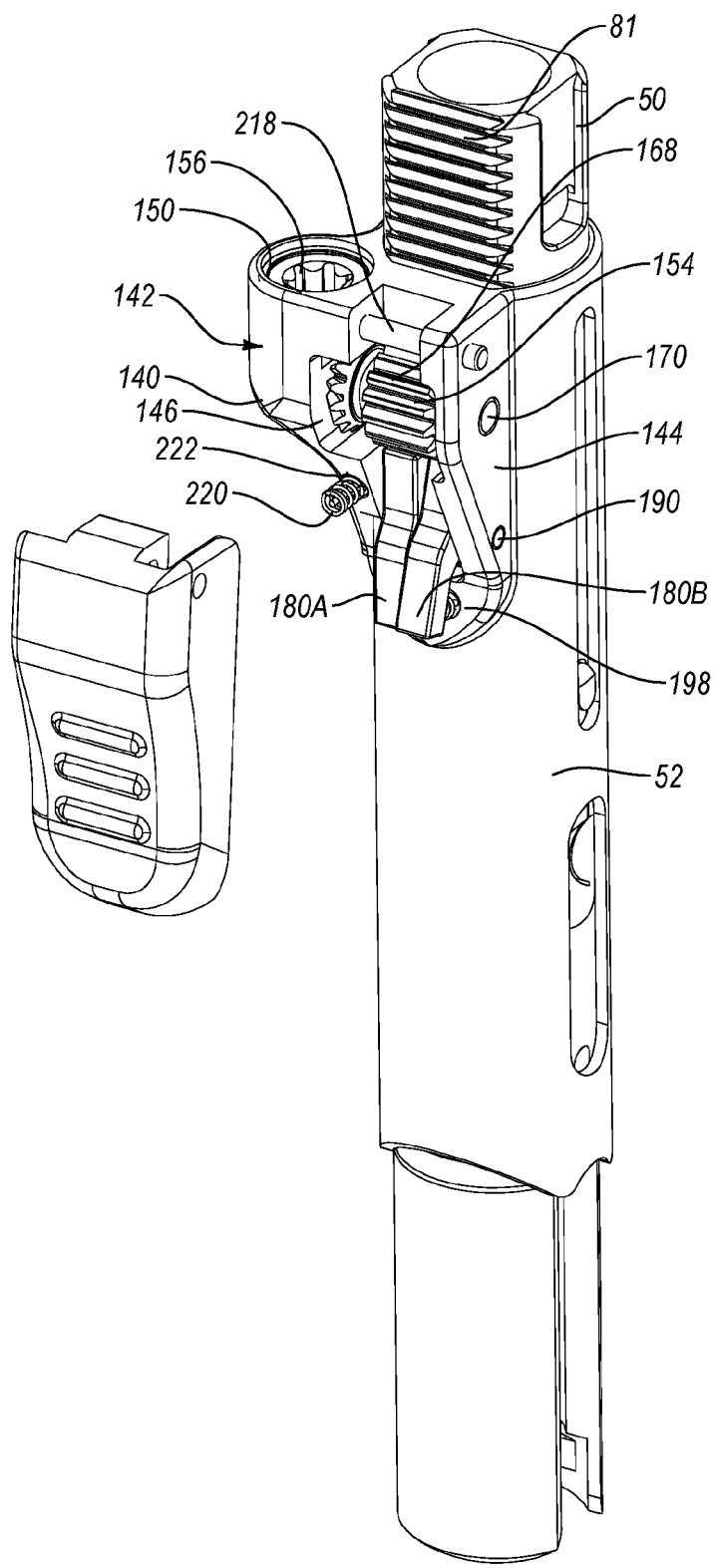
FIG. 11 is a partially exploded perspective view of the reduction jack showing the gear assembly attached to the reduction sleeve.
Figure 12:
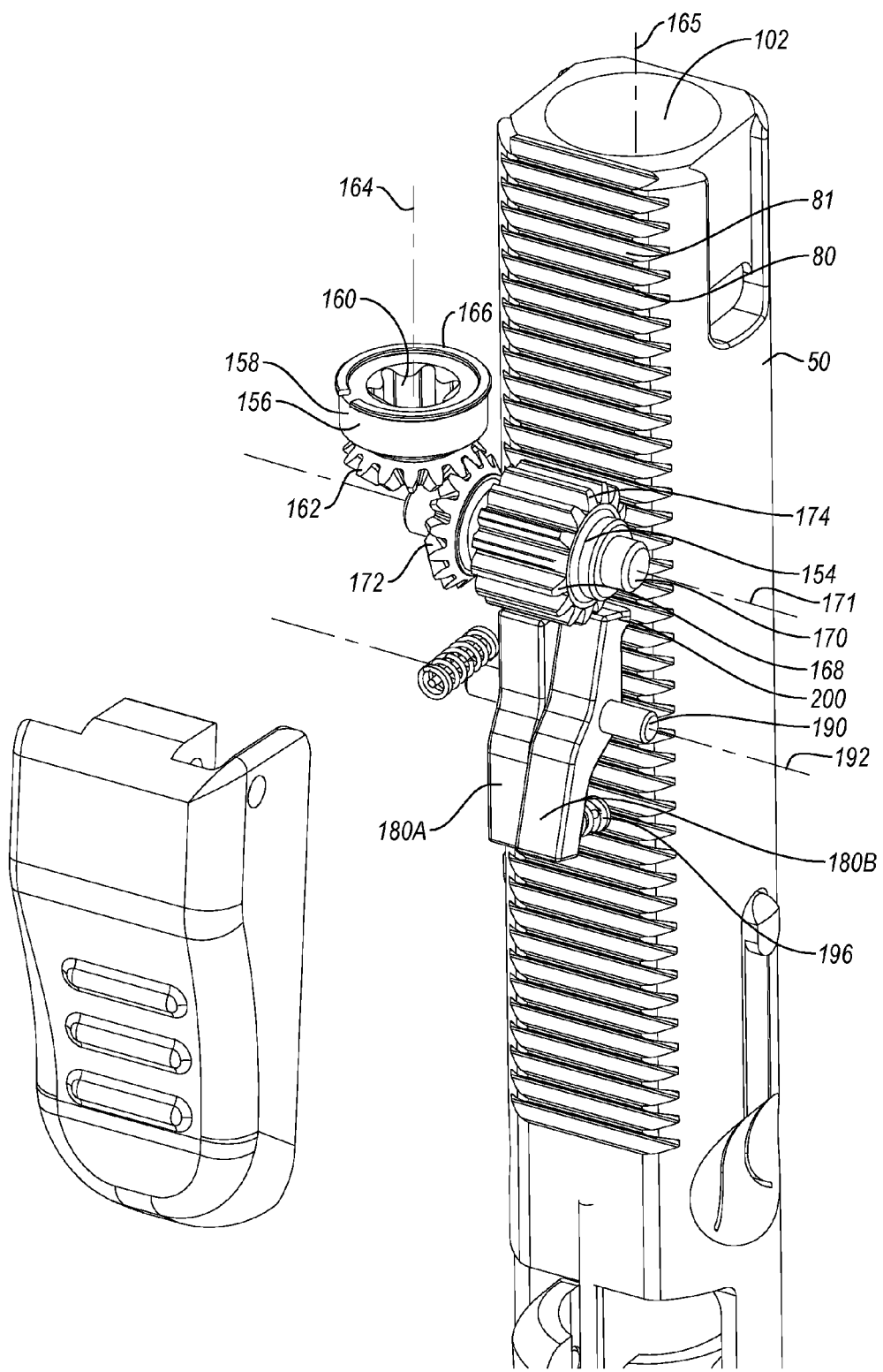
FIG. 12 is a perspective view showing how the gear assembly and pawls of FIG. 11 engage the teeth on the mounting stem.

Turning to FIGS. 11 and 12, mounted on housing 140 is a gear assembly 154. Gear assembly 154 comprises a first drive section 156 comprising a base 158 having a top surface with a drive socket 160 formed thereon. Drive socket 160 has a non-circular transverse cross section so that a driver can be received within drive socket 160 to facilitate rotation thereof. Base 158 has a bottom surface with a first bevel gear 162 formed thereon. Drive socket 160 and first bevel gear 162 have a common central axis 164 about which they rotate. Although not required, in this embodiment axis 164 is disposed parallel to a central longitudinal axis 165 extending through passageway 102 of mounting stem 50. Drive section 156 is rotatably received within pocket 150 of housing 140 so that first bevel gear 162 projects in compartment 146 through side opening 143. A C-shaped retention clip 166 retains drive section 156 within pocket 150 by being snapped fit within an annular recess formed on interior surface of pocket 150.

Gear assembly 154 further comprises a second drive section 168 that is disposed within compartment 146 of housing 140 and is rotatably mounted on an axle 170 that spans between arms 142 and 144. Second drive section 160 includes a second bevel gear 172 that is disposed orthogonal to first bevel gear 162 and which meshes with first bevel gear 162 so that rotation of first drive section 156 about axis 164 facilitates rotation of second drive section 168 about axis 171. Coupled with second bevel gear 172 is a pinion gear 174. Pinion gear 174 meshes with teeth 80 of rack 81 so as to form a rack and pinion gear system. That is, rotation of first drive second 162 causes concurrent rotation of second drive section 168 which, in turn, as a result of the engagement between pinion gear 174 and rack 81 causes reduction sleeve 52 to selectively travel in either direction along the length of mounting sleeve 50 depending on the direction of the rotation of first drive section 156. In one embodiment, the diameter of bevel gears 162 and 172 can be smaller than the diameter of pinion gear 174 resulting in a mechanical advantage in the rotation of pinion gear 174 and thus in the movement of reduction sleeve 52.

It is appreciated that a variety of alternative gear assemblies can be used for selectively moving reduction sleeve 52 along the length of mounting stem 50. The disclosed system, however, has the advantage that drive socket 160 is easy to access while passageway 102 remains unobstructed. Furthermore, the system permits a mechanical advantage through gear ratios as desired.

Figure 13:
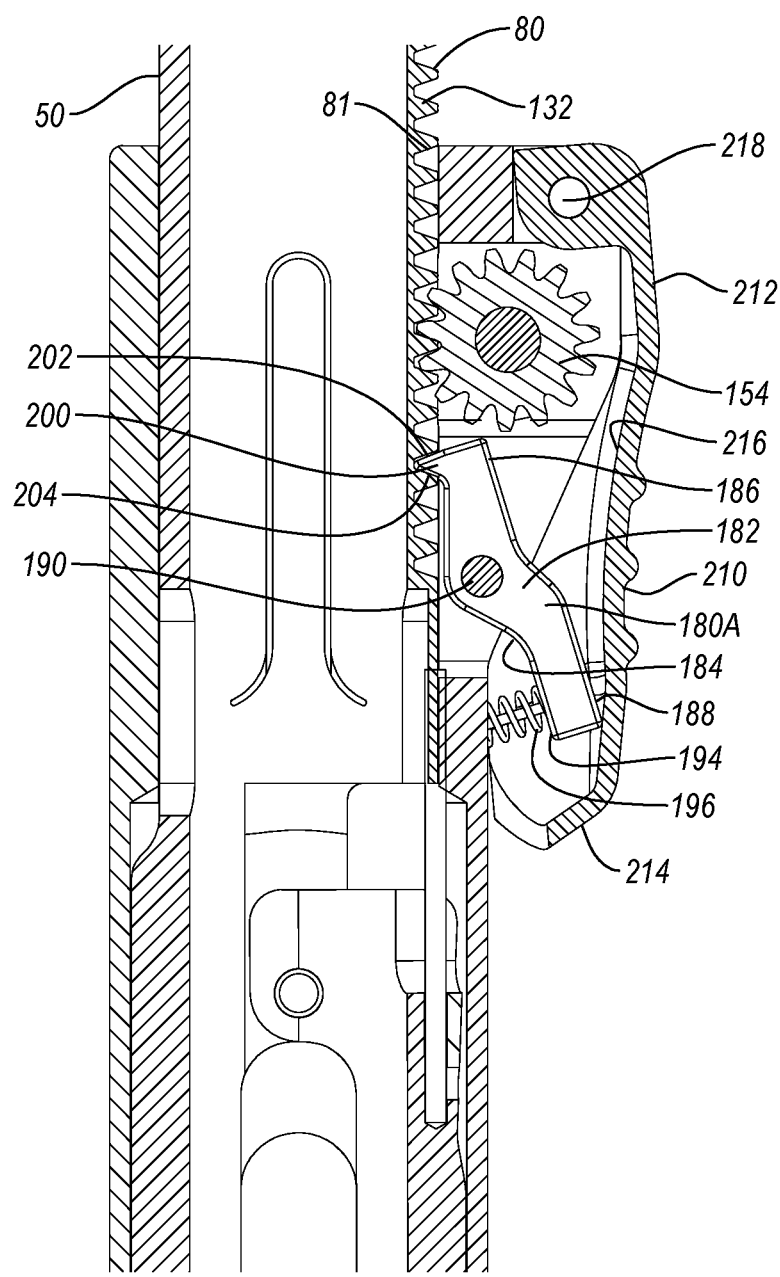
FIG. 13 is a cross sectional side view of the assembled reduction jack shown in FIG. 11.

Partially disposed within compartment 146 of housing 140 is a first pawl 180A and a second pawl 180B. As depicted in FIG. 13, pawl 180A comprises an elongated body 182 having an inside face 184 that extends between a first end 186 and an opposing second end 188. Pawl 180A pivots about an axle 190 that extends between and is secured to arms 142 and 144 of housing 140 (FIG. 11). Axle 190 has a central longitudinal axis 192 (FIG. 12) that is disposed parallel to axis 171 and perpendicular to axis 164. A pocket 194 is recessed on inside face 184 at second end 188. A spring 196 is received within pocket 194 and rests against a platform 198 (FIG. 11) of housing 140. Spring 196 applies a resilient force to pawl 180A that pushes pawl 180A into a forward rocked position.

Pawl 180A engages teeth 80 of rack 81 so as to form a ratchet. Specifically, forwardly projecting from inside face 184 at first end 186 is a tapered catch lip 200. Pawl 180A is configured so that when gear assembly 154 is rotated so as to move reduction sleeve 52 toward distal end 94 of mounting stem 50 (FIG. 4), catch lip 200 automatically rides over teeth 80 by pawl 180A moving from a forward rocked position to a rearward rocked position wherein spring 196 is compressed. As catch lip 200 passes over a tooth 80, pawl 180A resiliently moves back to the forward rocked position so that catch lip 200 is pressed back into the trough between the next pair of teeth 80. However, unless pawl 180A is manually moved to the rearward rocked position, catch lip 200 engages with teeth 80 to preclude reduction sleeve 52 from freely sliding towards proximal end 66 of mounting stem 50 (FIG. 4) even when gear assembly 154 is torqued for rotation in the opposite direction. Thus, pawl 180A permits reduction sleeve 152 to incrementally slide distally on mounting stem 50 through the manipulation of gear assembly 154 but restricts the movement of reduction stem 52 back towards the proximal end 66 of mounting stem 50.

As shown in FIG. 12, pawl 180B has substantially the same configuration as pawl 180A and is likewise biased toward the forward rocked position by a corresponding spring 196. Like elements between pawl 180A and 180B are identified by like reference characters. The only difference between pawl 180A and 180B is that the catch lips 200 of the two pawls 180 are offset so that they engage teeth 80 at different locations. Specifically, for example, when catch lip 200 of pawl 180A is disposed at the bottom of a trough between teeth 80, catch lip 200 of pawl 180B is disposed that the top of a tooth 80. This could be the same tooth, an adjacent tooth, or any other tooth. By using two pawls 180A and B in this configuration, reduction sleeve 52 can be advanced and held along mounting stem 50 at shorter intervals for more precise placement. That is, with only one pawl 180, reduction sleeve 52 can only be advanced and held at intervals of the width of one tooth 80. In contrast, by using two pawls 180A and B, reduction sleeve 52 can be advanced and held at intervals of one-half of the width of a tooth 80. It is appreciated that pawls 180 and teeth 80 can come in a variety of different configurations to produce the desired ratchet configuration.

As depicted in FIG. 4, a lever 210 is hingedly mounted to housing 140 of reduction sleeve 52 and extends over gear assembly 154 and pawls 180. As depicted in FIG. 13, lever 210 has a proximal end 212 and an opposing distal end 214 with an interior surface 216 extending therebetween. Proximal end 212 is hingedly coupled to a proximal end of housing 140 by an axle 218 extending between legs 142 and 144. A spring 220 (FIG. 11) is secured within a recess 222 formed on first leg 142 and biases against interior surface 216 of lever 210 to resiliently hold lever 210 in an extended position as shown in FIG. 13. When desired, distal end 214 of lever 210 can be radially inwardly pressed into a depressed position. In the depressed position, spring 220 is resiliently compressed and distal ends 188 of both pawls 180A and B are inwardly pushed by interior surface 216 of lever 210. Pawls 180A and B are thus moved into the rearward rocked position so that catch lips 200 are disengaged from teeth 80. As a result, with lever 210 manually depressed, pawls 180A and B are disengaged from teeth 80 permitting reduction sleeve 52 to freely slide either proximally or distally along mounting stem 50. Although pinion gear 174 remains engaged with teeth 80 while reduction sleeve 52 slides along mounting stem 50, pinion gear 174 freely rotates without hampering the movement of reduction sleeve. Once reduction sleeve 52 is in a desired position, lever 210 can be released which then resiliently moves back to the extended position, thereby causing pawls 180 to resiliently move back to the forward rocked position so as to engage teeth 80.

The method of using the assembled reduction jacks 10 will now be discussed in greater detail. Initially, as depicted in FIG. 1, bone fixation screws 14 are secured on opposing sides of adjacent vertebrae 15 which are desired to be fused together or otherwise stabilized or manipulated. Bone fixation screws 14 are typically threaded into the pedicles of each vertebra 15. Bone fixation screws 14 are typically attached with fastener 42 removed so that rod channels 28 are openly exposed. Next, spinal rod 40 having a desired contour for the positioning of vertebrae 15 is received within or is aligned with the corresponding rod channels 28 (FIG. 2) of the aligned bone fixation screws 14. Because spine rod 40 is rigid and some of the vertebrae are not in the desired orientation, spinal rod 40 will typically not nest within each of the rod channels 28. Where spinal rod 40 is received within a rod channel 28, a fastener 42 can be loosely attached to the corresponding collar 22 for capturing spinal rod 40 within the rod channel 28.

A reduction jack 10 is next secured to each bone fixation screw 14. Where spinal rod 40 is already received within a rod channel 28, it is not always necessary to secure a reduction jack 10 to that bone fixation screw 14. However, because reduction jacks 10 also assist in derotation of vertebrae 15, a reduction jack 10 is typically secured to all bone fixation screws 14. During the attachment of a reduction jack 10, reduction sleeve 52 is initially positioned proximally on mounting stem 50 so that reduction sleeve 52 is off of legs 90. Leg 90B thus resiliently pivots away from leg 90A. In this expanded configuration, legs 90 are advanced over collar 22 of bone fixation screw 14. Simultaneously, where spinal rod 40 is not already received within rod channel 28 of bone fixation screw 14, spinal rod 40 is also captured within rod channel 108 (FIG. 5) between legs 90.

Lever 210 of reduction sleeve 52 is then depressed releasing pawls 180 from teeth 80. Reduction sleeve 52 is then manually slide distally down mounting stem 50 so as to collapse legs 90 onto the opposing sides of collar 22. Legs 90 are positioned so that as they collapse into the closed position, catches 104A and B (FIG. 7) are received within retention notches 30A and B (FIG. 2) on collar 22 so that the reduction jack 10 is secured to the corresponding bone fixation screw 14. Reduction sleeve 52 is slid distally until spinal rod 40 captured within rod channel 108 is received within engagement grooves 134 (FIG. 9) located at the distal end of reduction sleeve 52.

Next, with legs 90 attached to collar 22 of bone fixation screw 14 and reduction sleeve 52 pushed against spinal rod 40, a driver is received within drive socket 160 (FIG. 12) of gear assembly 154 and rotated. As gear assembly 154 rotates, reduction sleeve incrementally moves distally along mounting stem 40, as discussed above, so as to reduce or move spinal rod 40 distally along rod channel 108 of mounting stem 50 and into rod channel 28 of the corresponding bone fixation screw 14. The mechanical advantage produced by gear assembly 154 assists in the reduction of spinal rod 40. When spinal rod 40 is sufficiently reduced into rod channel 28, a fastener 42 can be mounted onto collar 22 so as to capture spinal rod 40 within rod channel 28. Fastener 42 can be attached by placing fastener 42 on the end of a driver and then using the driver to pass fastener 42 down through passageway 102 of mounting stem 50 to collar 22. The driver can then be used to thread fastener 42 onto collar 22.

Once spinal rod 40 is captured within rod channel 28 of all bone fixations screws 14 and vertebrae 15 are all in the proper orientation, a driver can be used fully tighten fasteners 42 onto collars 22 so spinal rod 40 is securely fixed each bone fixation screw 14. In this configuration, the vertebrae 15 to which spinal rod 40 is attached are substantially precluded from moving relative to each other. Reduction jacks 10 can then be removed. The removal is accomplished by depressing lever 210 so as to release pawls 180 and then manually sliding reduction sleeve 52 proximately along mounting stem 50 until leg 90B resiliently outwardly pivots so as to release collar 22.

Reduction jacks 10 have a variety of unique benefits. For example, as a result of the ability to quickly release pawls 180, reduction sleeve 52 can be quickly advanced along mounting stem 50 and positioned against spinal rod 40 for subsequent reduction into rod channel 28 of bone fixation screw 14. One embodiment of the present invention thus enables rapid attachment of reduction jacks 10 to bone fixation screws 14, rapid reduction of spinal rod 40 and rapid removal of reduction jacks 10 from bone fixation screws 14. Furthermore, because gear assembly 154 remains engaged with teeth 80 when pawls 180 are released, there is less chance of misalignment of gear assembly 154 with teeth 80 throughout use. The use of two offset pawls 180A and B also permits greater precision in the positioning of reduction sleeve 52 and the reduction of spinal rod 40. Another benefit of one embodiment of the present invention is that gear assembly 154 and the driver socket thereon is openly exposed for easy attachment of a driver and thus easy movement of reduction sleeve 52. Other benefits also exist.

Figure 14:
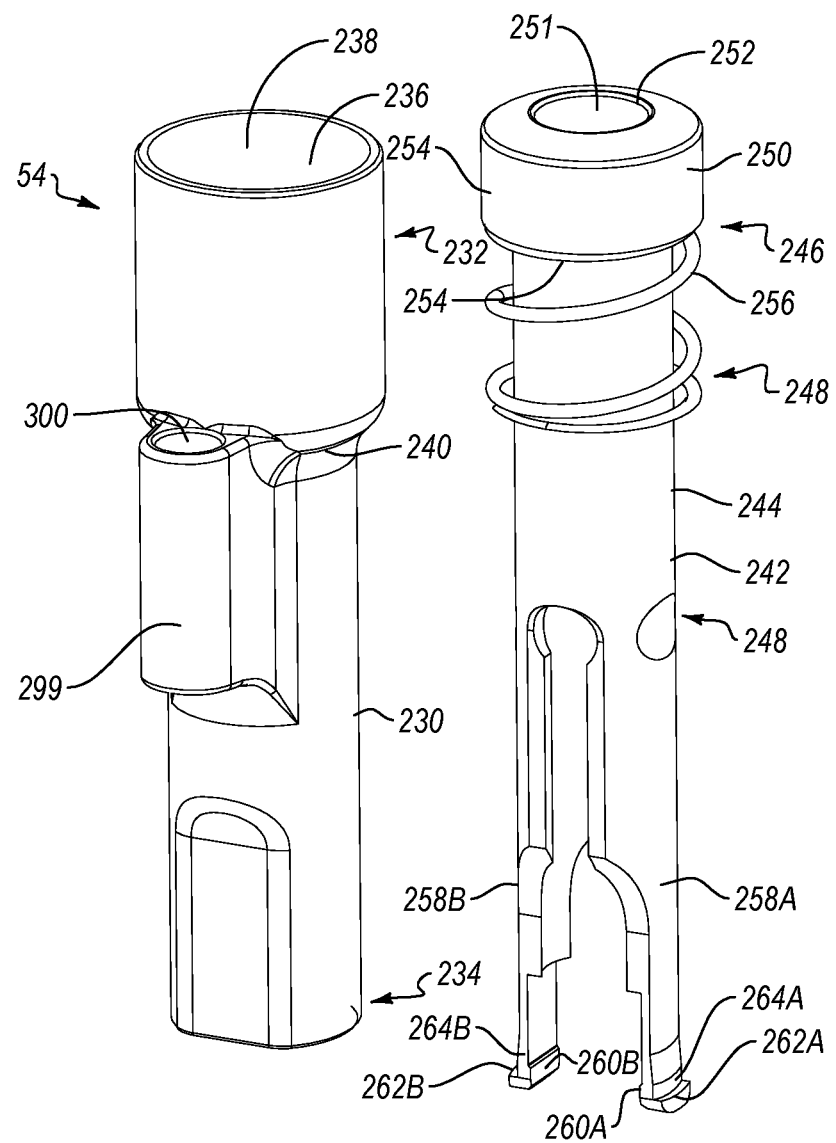
FIG. 14 is a partially exploded view of the extension of the reduction jack shown in FIG. 1.

With reference to FIG. 4, each reduction jack 10 can also include extension 54 that can removably couple to proximal end 66 of mounting stem 50. Extension 54 lengthens the reduction jack to permit greater leverage for manipulating vertebrae 15. The inventive reduction jacks can thus have different lengths depending on their needed use. As depicted in FIG. 14, extension 54 comprises an outer sleeve 230 having a proximal end 232 and an opposing distal end 234 and an interior surface 236 that bounds a passageway 238 extending therebetween. Interior surface 236 has a radially inwardly stepped shoulder 240. Outer sleeve 230 includes an outwardly projecting brace 299 having an opening 300 formed thereon.

A plunger 242 is configured to be received within passageway 238 of outer sleeve 230. Plunger 242 comprises a tubular body 244 having a proximal end 246 and an opposing distal end 248. Mounted on proximal end 246 is a cap 250 having an opening 252 that extends therethrough and communicates with passage 251. An annular gap recess 254 is formed between the bottom of cap 250 and body 244. A spring 256 is received within gap recess 254 and encircles body 244. A pair of mounting legs 258A and B project from a distal end 248 of tubular body 244. Radially inwardly projecting from distal end of each mounting leg 258A and B is a catch 260A and B, respectively. Likewise radially outwardly projecting from the distal end of each leg 258A and B is a retainer 262A and B, respectively. Also radially outwardly projecting from each leg 258A and B adjacent to retainers 262A and B is a tapered ramp 264A and B, respectively. Ramps 264 are disposed proximal to retainers 262 and slope radially outward as they extend toward retainers 262.

During assembly, the distal end of plunger 242 is advanced down through passageway 238 of outer sleeve 230 until spring 56 rests on inner shoulder 240. Distal end 234 of outer sleeve is configured to radially inwardly compress mounting legs 258 such that when retainers 262A and B pass beyond distal end 234 of outer sleeve 230, mounting legs 258 resiliently outwardly expand so that retainers 262 project over the distal end face of outer sleeve 230 and tapered ramps 264 rest against the interior surface of outer sleeve 230. In this configuration, retainers 262 prevent mounting legs 258 from unintentionally passing back up through passageway 238.

During attachment, as shown in FIG. 4, proximal end of plunger 242, i.e., cap 250, is manually depressed into distal end 232 of outer sleeve 230 by compressing spring 256 therein. As a result, mounting legs 258 distally project further beyond distal end 234 of outer sleeve 230. As mounting legs 258 move further distally, ramps 264 are moved outside of outer sleeve 230 which enables mounting legs 258 to further separate. The exposed separated legs 258 are then slidably received within corresponding alignment channels 82 on proximal end 66 of mounting stem 50 so that catches 260A and B are received within corresponding pockets 84A and B. Plunger 242 is then released forcing distal end 234 of outer sleeve 230 to encircle proximal end 66 of mounting stem 50 and to pass over ramps 264. As outer sleeve 230 passes over ramps 264, legs 258 are radially inwardly compressed so as to lock catches 260 into pockets 84 and thereby lock extension 54 to mounting stem 50. To remove extension 54, the process is reverse. The attachment of extension 54 to mounting stem 50 gives greater length to reduction jacks 10 which allows greater leverage for derotation or other manipulation of vertebrae 15 that may be out of alignment. In alternative embodiments, it is appreciated that extension 54 could be attached to mounting stem 50 using a variety of other techniques.

In the assembled configuration, passage 251 extending through plunger 242 aligns with passageway 102 extending through mounting stem 50 so that a driver with fastener 42 thereon can be passed through the entire length of extension 54 and mounting stem 50. Extension 54 typically has a length in a range between 4 cm and 15 cm with between 5 cm and 12 cm being more common. Other lengths can also be used.

Figure 15:
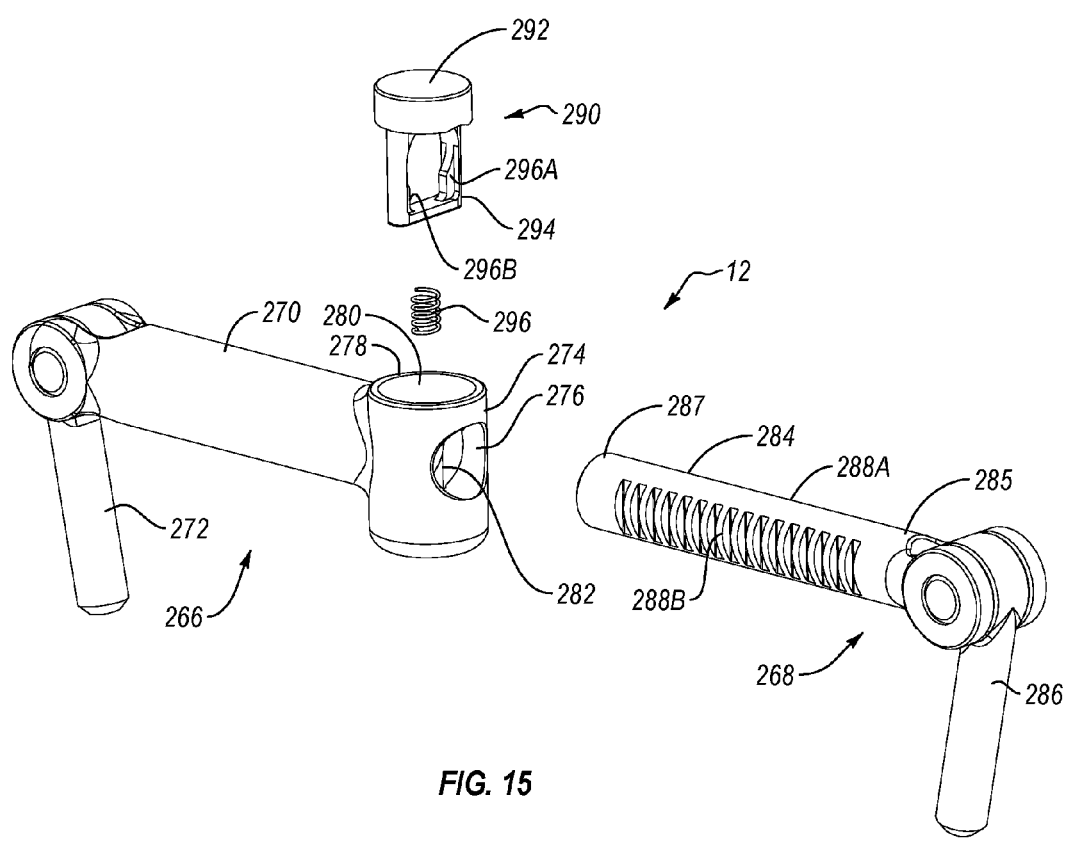
FIG. 15 is an exploded view of the bridge of the reduction jack shown in FIG. 1.

As depicted in FIG. 1, where desired, bridge 12 can extend between extensions 54 of adjacent reduction jacks 10 to help facilitate stabilization and desired orientation of the reduction jacks 10 and the corresponding vertebrae 15. As depicted in FIG. 15, bridge 12 comprises a first brace 266 and a second brace 268 that can be mounted to corresponding extensions 54 and which can be adjustably telescoped relative to one another to be fixed in a desired length. First brace 266 comprises a tubular shaft 270 having a first end with a coupling pin 272 hingedly mounted thereat and an opposing second end with a housing 274 mounted thereat. Coupling pin 272 can be removably received within opening 300 on extension 54 (FIG. 14) for securing first brace 266 to extension 54. A passageway 276 laterally extends through housing 274 and along the length of shaft 270. Housing 274 has a top end 278 with an opening 280 formed thereat that communicates with passageway 276. Formed on the interior surface of housing 274 adjacent to passageway 276 is a channel 282.

Second brace 268 comprises a shaft 284 having a first end with a coupling pin 286 hingedly coupled thereto and an opposing second end 287. Coupling pin 286 can be removably received within opening 300 on of a corresponding extension 54 (FIG. 14) for securing second brace 268 to an extension 54. Formed along each opposing side of shaft 284 along the length thereof are a plurality of locking slots 288. Shaft 284 is configured to telescope into and out of passageway 276 of shaft 270.

An engager 290 is configured to lock together shafts 270 and 284 at desired telescoped positions. Engager 290 comprises a button 292 having a U-shaped frame 294 projecting therefrom. Inwardly extending from the lower end of frame 294 are a pair of opposing flanges 296A and B. Frame 294 is configured to be slidably received within channel 282 of housing 274. A spring 298 is placed between a floor of housing 274 and the bottom of frame 294 to resiliently upwardly bias engager 290. By downwardly pressing on button 292 engager 290 is moved to a depressed position wherein shaft 284 can freely telescope into and out of passageway 276 of shaft 270. When shafts 270 and 284 are in their desired position, button 292 can be released. Spring 296 then upwardly pushes engager 290 so that flanges 296A and B are received within corresponding locking slots 288A and B on shaft 284, thereby locking shaft 284 at a desired telescoped position within passageway 276.

It is appreciated that housing 274 and engager 290 can be replaced with a variety of different configurations so as clamps, fasteners, set screws, and the like for securing braces 266 and 268 as relative positions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A reduction jack for placing a spinal rod within a rod channel of a bone fixation screw, comprising:
    an elongated, tubular, mounting stem comprising:
        a tubular body;
        a plurality of teeth disposed on the body;
        a pair of legs attached to and projecting from the body, at least a portion of the legs being separated by two spaced apart rod channels; and
        means disposed on the legs for engaging the bone fixation screw;
    a reduction sleeve at least partially encircling the mounting stem, the reduction sleeve having a proximal end and an opposing distal end; and
    a first pawl pivotably mounted to the reduction sleeve and resiliently biased against the teeth on the body, the first pawl being pivotable between a first position where the first pawl engages the teeth on the body and a second position wherein the first pawl does not engage the teeth on the body.

2. The reduction jack as recited in claim 1, further comprising a lever mounted on the reduction sleeve, the lever being movable between a first position where the first pawl engages the teeth on the body and a second position wherein the first pawl does not engage the teeth on the body.

3. The reduction jack as recited in claim 2, wherein the reduction sleeve can freely slide in either direction along the length of the mounting stem when the lever is in the second position.

4. The reduction jack as recited in claim 1, further comprising a second pawl pivotably mounted to the reduction sleeve and resiliently biased against the teeth on the body, the second pawl being offset from the first pawl so that the first and second pawl either simultaneously engage different teeth or simultaneously engage different sides of the same tooth.

5. The reduction jack as recited in claim 4, further comprising a lever mounted on the reduction sleeve, the lever being movable between a first position where the first pawl and second pawl engage the teeth on the body and a second position wherein the first pawl and second pawl do not engage the teeth on the body.

6. The reduction jack as recited in claim 1, wherein at least one of the legs of the mounting stem is hingedly coupled to the body.

7. The reduction jack as recited in claim 6, wherein the reduction sleeve can be moved between a first position which permits the at least one of the legs to outwardly pivot and a second position which prevents the at least one of the legs from outwardly pivoting.

8. The reduction jack as recited in claim 1, wherein the means for engaging the bone fixation screw comprises a catch inwardly projecting from an interior surface of each leg.

9. The reduction jack as recited in claim 1, further comprising a gear assembly, the gear assembly comprising:
    a first gear engaging the teeth on the body;
    a second gear connected to the first gear; and
    a driver socket formed on the second gear such that rotation of the drive socket facilitates rotation of the second gear which in turn rotates the first gear, the gears being configured to produce a mechanical advantage.

10. The reduction jack as recited in claim 1, further comprising an extension removably coupled to the mounting stem.

11. A spine fixation system comprising:
- a bone fixation screw having a rod channel formed thereon;
- an elongated spinal rod received within the rod channel of the bone fixation screw; and
- reduction jack comprising:
  - an elongated, tubular, mounting stem comprising:
    - a tubular body;
    - a plurality of teeth disposed on the body; and
    - a pair of legs attached to and projecting from the body and being removably coupled to the bone fixation screw;
  - a reduction sleeve at least partially encircling the tubular stem, the reduction sleeve having a proximal end and an opposing distal end, the distal end being biased against the spinal rod; and
  - a first pawl pivotably mounted to the reduction sleeve and resiliently biased against the teeth on the body, the first pawl being pivotable between a first position where the first pawl engages the teeth on the body and a second position wherein the first pawl does not engage the teeth on the body.

12. The spine fixation system as recited in claim 11, further comprising a lever mounted on the reduction sleeve, the lever being movable between a first position where the first pawl engages the teeth on the body and a second position wherein the first pawl does not engage the teeth on the body, wherein the reduction sleeve can freely slide in either direction along the length of the mounting stem when the lever is in the second position.

13. A method for operating a spinal reduction jack, the method comprising:
- coupling a distal end of a tubular mounting stem to a bone fixation screw having a rod channel formed thereon, the distal end of a tubular mounting stem having a pair of rod channels formed thereon in which a spinal rod is received;
- moving a lever on a reduction sleeve that at least partially encircles the mounting stem to a second position so that a first pawl disengages from teeth on the mounting stem;
- with the lever in the second position, freely sliding the reduction sleeve along a length of the mounting stem so that a distal end of the reduction sleeve is disposed against or adjacent to the spinal rod;
- moving the lever to a first position so that the first pawl engages the teeth; and
- manipulating the reduction sleeve so that the distal end of the reduction sleeve reduces the spinal rod into the rod channel of the bone fixation screw.

14. The method as recited in claim 13, further comprising passing the shaft of a driver down through the mounting stem and coupling a fastener on the shaft to the bone fixation screw so as to secure the spinal rod within the rod channel of the bone fixation screw.

15. The method as recited in claim 13, wherein moving the lever to the second position causes the first pawl and a second pawl to disengage from the teeth on the mounting stem.

16. The method as recited in claim 13, further comprising:
- moving the lever back to the second position after the spinal rod has been reduced into the rod channel; and
- freely sliding the reduction sleeve on the mounting stem away from the spinal rod.

\* \* \* \* \*